(12) United States Patent
Eckert

(10) Patent No.: US 7,825,167 B2
(45) Date of Patent: Nov. 2, 2010

(54) DENTAL COMPOSITION CONTAINING UNSATURATED HALOGENATED ARYL ALKYL ETHER COMPONENTS

(75) Inventor: Adrian S. Eckert, Munich (DE)

(73) Assignee: 3M Espe AG, Seefeld (DE)

( * ) Notice: Subject to any disclaimer, the term of this patent is extended or adjusted under 35 U.S.C. 154(b) by 540 days.

(21) Appl. No.: 11/572,067

(22) PCT Filed: Jul. 14, 2004

(86) PCT No.: PCT/EP2004/007747

§ 371 (c)(1), (2), (4) Date: Jan. 12, 2007

(87) PCT Pub. No.: WO2006/005364

PCT Pub. Date: Jan. 19, 2006

(65) Prior Publication Data

US 2008/0051488 A1    Feb. 28, 2008

(51) Int. Cl.
*A61K 6/08* (2006.01)
*C08F 283/12* (2006.01)
*C08G 77/04* (2006.01)

(52) U.S. Cl. .......... 522/172; 522/99; 522/148; 522/181; 522/908; 523/109; 523/115; 523/116; 523/118; 523/300; 525/479; 528/26

(58) Field of Classification Search .......... 523/109, 523/116, 118, 300, 115; 522/99, 148, 172, 522/181, 908; 525/479; 528/26
See application file for complete search history.

(56) References Cited

U.S. PATENT DOCUMENTS

| | | | |
|---|---|---|---|
| 2,488,500 A * | 11/1949 | Moyle | 568/643 |
| 3,715,334 A | 2/1973 | Karstedt | |
| 3,775,352 A | 11/1973 | Leonard | |
| 3,814,730 A | 6/1974 | Karstedt | |
| 3,933,880 A | 1/1976 | Bergstrom et al. | |
| 3,971,754 A | 7/1976 | Jurecic | |
| 4,391,590 A | 7/1983 | Dougherty | |
| 4,705,836 A | 11/1987 | Ohtsuka et al. | |
| 4,766,176 A * | 8/1988 | Lee et al. | 525/100 |
| 4,767,798 A | 8/1988 | Gasser et al. | |
| 4,788,268 A | 11/1988 | Lau et al. | |
| 5,145,886 A | 9/1992 | Oxman et al. | |
| 5,165,890 A | 11/1992 | Discko | |
| 5,233,006 A * | 8/1993 | Wolter et al. | 528/32 |
| 5,322,440 A | 6/1994 | Steele | |
| 5,750,589 A | 5/1998 | Zech et al. | |
| 5,824,712 A * | 10/1998 | Willkomm et al. | 521/135 |
| 6,046,250 A | 4/2000 | Boardman et al. | |
| 6,084,004 A | 7/2000 | Weinmann et al. | |
| 6,376,569 B1 | 4/2002 | Oxman et al. | |
| 6,387,981 B1 | 5/2002 | Zhang et al. | |
| 6,566,413 B1 | 5/2003 | Weinmann et al. | |
| 6,572,693 B1 | 6/2003 | Wu et al. | |
| 6,624,236 B1 | 9/2003 | Bissinger et al. | |
| 6,653,375 B2 | 11/2003 | Moszner et al. | |
| 7,241,856 B2 * | 7/2007 | Jin et al. | 528/301 |
| 2002/0010103 A1 | 1/2002 | Takayama et al. | |
| 2005/0252413 A1 | 11/2005 | Kangas et al. | |
| 2005/0252414 A1 | 11/2005 | Craig et al. | |
| 2005/0256223 A1 | 11/2005 | Kolb et al. | |

FOREIGN PATENT DOCUMENTS

| | | | |
|---|---|---|---|
| EP | 0238025 A1 | | 9/1987 |
| EP | 0451702 A2 | | 10/1991 |
| EP | 0480238 A | | 4/1992 |
| EP | 0897710 A1 | | 2/1999 |
| JP | 61027992 | | 2/1986 |
| JP | 61-027992 | * | 7/1986 |
| WO | WO 98/22521 | | 5/1998 |
| WO | WO 98/33645 | | 8/1998 |
| WO | WO 98/47046 | | 11/1998 |
| WO | WO 98/47047 | | 11/1998 |
| WO | WO 99/62894 | | 12/1999 |
| WO | WO 00/19967 | | 4/2000 |
| WO | WO 01/30305 | | 5/2001 |
| WO | WO 01/30306 | | 5/2001 |
| WO | WO 01/30307 | | 5/2001 |
| WO | WO 01/92271 A1 | | 12/2001 |
| WO | WO 01/95862 A1 | | 12/2001 |
| WO | WO 02/066535 | | 8/2002 |
| WO | WO 03/063804 | | 8/2003 |

(Continued)

OTHER PUBLICATIONS

STIC Search Report , p. 1-14, JP 61-027992, Kawashima et al.*

(Continued)

*Primary Examiner*—Mark Eashoo
*Assistant Examiner*—Jessica Paul
(74) *Attorney, Agent, or Firm*—Ann Mueting

(57) ABSTRACT

The invention relates to a dental composition comprising a) halogenated aryl alkyl ether component (A) comprising at least 1 aryl alkyl ether moiety, at least 1 halogen atom attached to each aryl residue of the aryl alkyl ether moieties, at least 2 unsaturated moieties, b) Si—H functional component (B), c) initiator (C), d) optionally filler (D), and e) optionally component (E) selected from modifiers, dyes, pigments, thixotropic agents, flow improvers, polymeric thickness, surfactants, odorous substances, diluting agent(s) and flavourings.

29 Claims, No Drawings

FOREIGN PATENT DOCUMENTS

| | | |
|---|---|---|
| WO | WO 2006/005364 | 1/2006 |
| WO | WO 2006/005365 A1 | 1/2006 |

OTHER PUBLICATIONS

Houben-Weyl, Methoden d. Organischen Chemie, vol. VI/3, p. 385-405., Georg Thieme Verlag, Stuttgart, 1965, 4. edition.

Houben-Weyl, Methoden d. Organischen Chemie, vol. VI/3, p. 57 (first preparation example) resp. p. 56 (first prep. Example), Georg Thieme Verlag, Stuttgart, 1965, 4. edition.

OECD Guideline 471 and ISO 10993-3 (2003).

Tarbell et al., The Rearrangement of 4-Crotyloxy-3,5-Dichlorobenzoic Acid, *J. Am. Chem. Soc.*, 1942, 64(5), 1066-1070.

Marciniec, B., Comprehensive Handbook on Hydrosilylation, p. 8-98., Pergamon Press, Oxford, 1992.

Houben-Weyl, Methoden d. Organ. Chemie, vol. VI/3, p. 49ff., Georg Thieme Verlag, Stuttgart, 1965, 4. edition.

EN ISO 4049.

DIN EN 9917-1.

DIN EN 9917-2.

\* cited by examiner

DENTAL COMPOSITION CONTAINING UNSATURATED HALOGENATED ARYL ALKYL ETHER COMPONENTS

CROSS REFERENCE TO RELATED APPLICATIONS

This application is a national stage filing under 35 U.S.C. 371 of PCT/EP2004/007747, filed Jul. 14, 2004.

The invention relates to a curable dental composition containing an unsaturated halogenated aryl alkyl ether component. The composition has improved properties and can be used e.g. as a dental filling material.

The dental filling materials on the market can generally be divided into composites, resin modified glass ionomer cements and glass ionomer cements (GIZ). The composites cure usually via a light induced radical polymerisation of unsaturated components, especially (meth)acrylates. The glass ionomer cements cure by a cement setting reaction, whereas the resin modified glass ionomer cements both curing is achieved using both mechanisms.

Of special interest are the dental composites, the curing of which results in a very hard material compared to the glass ionomer cements which is especially useful for filling teeth cavities. However, a well known disadvantage of the dental composites on the market is that the compositions shrink on curing. A further drawback is, that some of the components of the dental composite materials are not hydrolytically very stable and/or comparable hydrophilic and thus harmful substances can emerge from the cured composition over the years.

Attempts were made to solve the above mentioned problems.

In this respect U.S. Pat. No. 6,653,375 B2 describes urethane di(meth)acrylate derivatives of 1,3-bis(1-isocyanato-1-lmethylethyl)benzene. It is stated that the monomers have a refractive index compatible with that of customary dental filling materials, do not tend towards discolorations and can replace bis-GMA in dental materials without impairing the mechanical properties of the materials.

U.S. Pat. No. 6,624,236 B1 is directed to cyclosiloxane-based crosslinkable monomers, production thereof and use thereof in polymerisable materials, in particular to polysiloxanes from sol-gel-condensable cyclosiloxane (meth)acrylates as well as resinous compositions.

U.S. Pat. No. 6,566,413 B1 relates to polymerisable materials based on hardenable siloxane compounds useful for dental compositions. It is described that the siiloxane compounds used display a low viscosity, permit a high filler uptake and lead to compositions with a low polymerisation shrinkage.

In WO 01/92271 A1 prepolymeric (meth)acrylates with polycyclic or aromatic segments are described useful for the preparation of dental materials. It is said that the siloxane monomers have a high molecular weight (e.g. over 600 g/mol), have a high (meth)acrylate functionality and a low visclosity.

WO 01/095862 A1 refers to a low shrinking polymerisable dental material including a mixture of di- or poly(meth)acrylate, an alkoxylated bisphenol dimethacrylate, a polymerisable monomer, a polymerisation initiator and/or sensitizer, a stabilizer and a filler. It is mentioned that the volumetric shrinkage during polymerisation is less than 2 Vol-%.

EP 0 451 709 A2 discloses silanes of a certain formula which can comprise groups containing (meth)acrylate moieties. It is stated that the silanes can be used as such or as additives for coating compositions, bulk materials, adhesives and compositions for injection moulding.

The solutions described above however are not completely satisfying.

Therefore, there is a need for alternatives. There is especially a need for alternative materials with improved properties.

It is thus an object of the present invention to alleviate one or more of the problems mentioned above.

It is also an object of the present invention to provide an esthetical composition if used in the dental field.

It is another object of the present invention to provide a lipophilic composition.

It is another object of the present invention to provide a composition with improved properties, especially a composition which enables one to provide a composition having a low shrinkage value.

It has been found that one or more of the above mentioned objects can be achieved by providing a composition as described in the text below.

Surprisingly, it has been found that using halogenated aryl alkyl ether derivatives comprising polymerizable groups such as unsaturated groups enables one to provide curable dental compositions with improved properties.

Thus, the present invention relates to a dental composition comprising a) halogenated aryl alkyl ether component (A) comprising
   at least 1 aryl alkyl ether moiety,
   at least 1 halogen atom attached to each aryl residue of the aryl alkyl ether moieties,
   at least 2 unsaturated moieties,
b) Si—H functional component (B),
c) initiator (C),
d) optionally filler (D),
e) optionally component (E) selected from modifiers, dyes, pigments, thixotropic agents, flow improvers, polymeric thickeners, surfactants, odorous substances, diluting agent(s) and flavourings.

The present invention also relates to a method of producing the composition as described below.

Additionally, the present invention relates to a method of using the composition as described below.

The halogenated aryl alkyl ether component (A) can be used alone or in a mixture with other unsaturated components as reactive compounds in dental materials that may also contain other reactive and/or unreactive compounds, if needed.

The halogenated aryl alkyl ether component (A) often show a comparably high refractive index together with a comparably low viscosity so that the dental compositions provided might have an excellent opacity and thus are highly esthetic. Moreover, the compositions often show comparably low shrinkage as well as low uptake of water and/or water soluble dyes (e.g. from coffee, tea, red wine) after curing- compared to other dental compositions on the market.

The terms "comprise" and "contain" within the meaning of the invention introduce a non exhaustive list of features. Likewise, the word "one" or "a" is to be understood in the sense of "at least one".

The term "dental composition" according to the invention is a curable composition to be used in the dental field for different purposes, usually in small amounts of a few grams.

The term "Si—H functional component" according to the invention is a substance or mixture of substances each containing at least 1 Si atom and at least 1 H atom directly attached to a Si atom within the molecule.

The term "initiator" according to the invention is a substance or mixture of substances capable of starting a curing reaction, preferably a hydrosilylation curing reaction.

The term "unsaturated moiety" according to the invention refers to a moiety which is polymerisable, especially via a hydrosilylation reaction, comprising preferably a terminal olefinic group.

Halogenated aryl alkyl ether component (A) can be synthesized e.g. via an etherification reaction (e.g. Houben-Weyl, Methoden der Organischen Chemie, volume VI/3, p49ff., Georg Thieme Verlag, Stuttgart, 1965, 4. edition) of a phenolic precursor.

The etherification reaction is a nucleophilic substitution reaction where a phenolic nucleophile (i) is substituting a leaving group LG of an electrophile (ii) as indicated in scheme (I) forming a new C—O single bond and yielding an ether compound (iii):

$$\text{scheme (I)}$$

$$_1R\text{—}O^- + \,_3R\text{—}\underset{_4R}{\overset{_2R}{C}}\text{—}LG \longrightarrow \,_3R\text{—}\underset{_4R}{\overset{_2R}{C}}\text{—}O\text{—}_1R$$

(i)             (ii)                          (iii)

wherein $R_1$=aromatic or (cyclo)aliphatic aromatic moiety, wherein C and/or H atoms can also be substituted by e.g. 0, Br, and Cl atoms, $R_2$, $R_3$, $R_4$=aliphatic or aromatic moiety, wherein C and/or H atoms can also be substituted by e.g. 0, Br, and Cl atoms.

That is, the halogenated aryl alkyl ether component (A) of the invention can be obtained via an etherification reaction according to scheme (I) by reacting phenolic precursor (i) with electrophile (ii) as described e.g. for aryl alkyl ether compounds like Allyl-phenyl-ether or But-2-enyl-(2-methoxy-phenyl)-ether in Houben-Weyl, Methoden der Organischen Chemie, volume VI/3, p 57 (first preparation example) or p 56 (first preparation example), Georg Thieme Verlag, Stuttgart, 1965, 4. edition or like Allyl-(2-chloro-phenyl)-ether as e.g. described by Tarbell, D., S., Wilson, J., W., J. Am. Chem. Soc. 1942, 64(5), 1066-1070. Possible phenolic precursors (i) like 2,2-Bis[3,5-dichloro-4-hydroxy-phenyl]-propane or 2,2-Bis[3,5-dibromo-4-hydroxy-phenyl]-propane are commercially available or can be synthesized like 2-Allyl-6-chloro-phenole as e.g. described by Tarbell, D., S., Wilson, J., W., J. Am. Chem. Soc. 1942, 64(5), 1066-1070.

Possible electrophiles (ii) like 3-Bromo-propene, 4-Bromo-butene, 5-Bromo-pentene, or 6-Bromo-hexene are commercially available.

Halogenated aryl alkyl ether component (A) of the inventive composition preferably comprises the following chemical moieties:

aryl alkyl ether moieties: 1, 2, 3 or 4
halogen atoms attached to the aryl residue of each aryl alkyl ether moieties: at least 1, 2, 3 or 4
unsaturated moieties: at least 2, 3 or 4.

The halogenated aryl alkyl ether component (A) of the inventive composition usually does not comprise Si-Atoms.

The amount of halogenated aryl alkyl ether component (A) can be as low as about 1 wt.-%, or as low as about 3 wt.-%, or as low as about 10 wt.-% with respect to the cured composition.

The amount of halogenated aryl alkyl ether component (A) can be can be as high as about 90 wt.-%, or as high as about 65 wt.-%, or as high as about 30 wt.-% with respect to the cured composition.

The amount of Si—H functional component (B) can be as low as about 1 wt.-%, or as low as about 3 wt.-%, or as low as about 10 wt.-% with respect to the cured composition.

The maximum amount of Si—H functional component (B) can be can be as high as about 90 wt.-%, or as high as about 65 wt.-%, or as high as about 30 wt.-% with respect to the cured composition.

The amount of initiator (C) can be as low as about 0.00005 wt.-%, or as low as about 0.0002 wt.-%, or as low as about 0.002 wt.-% with respect to the cured composition and calculated as elemental metal and related to the overall weight of the material present regarding compounds (A) to (E).

The amount of initiator (C) can be can be as high as about 1.0 wt.-%, or as high as about 0.5 wt.-%, or as high as about 0.1 wt.-% with respect to the cured composition and calculated as elemental metal and related to the overall weight of the material present regarding compounds (A) to (E).

The amount of optional filler (D) can be as low as about 3 wt.-%, or as low as about 25 wt.-%, or as low as about 50 wt.-% with respect to the cured composition.

The amount of optional filler (D) can be as high as about 90 wt.-%, or as high as about 80 wt.-%, or as high as about 75 wt.-% with respect to the cured composition.

Optional component (E) can be present up to an amount of about 25 wt.-%, or up to an amount of about 15 wt.-%, or up to an amount of about 3 wt.-% with respect to the cured composition.

The dental composition of the invention meets preferably at least one of the following characteristics:

The viscosity of halogenated aryl alkyl ether component (A) can be equal or above about 0.1 Pa*s, or equal or above about 1 Pa*s, or equal or above about 2 Pa*s.

The viscosity of halogenated aryl alkyl ether component (A) usually does not exceed about 80 Pa*s, can be equal or below about 20 Pa*s, or can be equal or below about 5 Pa*s.

The refractive index of halogenated aryl alkyl ether component (A) can be equal or above about 1.530, or equal or above about 1.560, or equal or above about 1.590.

The refractive index of halogenated aryl alkyl ether component (A) usually does not exceed about 1.680, can be equal or below about 1.650, or equal or below about 1.620.

The opacity of the cured dental composition can be equal or above about 10%, or equal or above about 40%, or equal or above about 70%.

The opacity of the cured dental composition usually does not exceed 92%, can be equal or below about 90%, or equal or below about 88%.

The molecular mass (Mw) of halogenated aryl alkyl ether component (A) can be equal or above about 400, or equal or above about 600, or equal or above about 800.

The molecular mass (Mw) does usually not exceed about 10.000, can be equal or below 5.000, or equal or below about 2.000.

If not indicated otherwise, the measurements were done at standard temperature and pressure ("STP", i.e. 23° C. and 1023 hPa) according to the methods described below.

The refractive index of carbosilane containing component (A) is measured with a Kruess AR 4 D device (refractometer according to Abbe's measure principle). The refractive index is measured at 20.0° C. The refractive index is measured at a wavelength of 589 nm.

The viscosity of carbosilane containing component (A) is measured with a Haake RotoVisco RV1 device (rotor C60/1 for viscosities up to 8000 mPa*s or rotor C20/1 for viscosities above 8000 mPa*s together with stator P61). The viscosity is measured at 23.0° C. between two plane and parallel plates (i.e. stator and rotor). After activation and rectification of the system, the appropriate rotor is installed. Then the rotor is lowered and the distance between stator and rotor is adjusted to 0.052 mm (using Software RheoWin Pro Job Manager Software Version 2.94} for the viscosity measurement. Then the rotor is lifted and the material to be measured is put on the stator (1.0 ml with rotor C60/1 or 0.04 ml with rotor C20/1). Without undue delay, the rotor is lowered back to the preliminary adjusted measuring position. The material to be measured is tempered at 23.0° C. The shear rate for the measurement is adjusted to a value that produced a torque of at least 5000 µNm (therefore normally shear rates of 100, 200, 500, or 1000 $s^{-1}$ are used depending on the viscosity of the material to be measured). The measurement is started and run for 60 s. The viscosity values (Pa*s) are recorded 20 s after the start of measurement and the mean value of the recorded values is given as viscosity.

The molecular weight ($M_w$) of carbosilane containing component (A) is determined with GPC. Appropriate methods are know by the expert. In addition the determination of the molecular weight is possible using nuclear magnetic resonance spectroscopy (end-group determination).

The opacity of the cured dental composition is measured by means of specimens with a defined height of 3.6 (+/−0.1) mm and a diameter of 20 (+/−0.1) mm. These are prepared by filling the material to be checked into suitably high rings, evenly and free of bubbles, and curing it chemically by storing it at standard temperature or 50° C. over night between plane, transparent, silicone oil treated glass slides. The opacity is then measured with the colour measuring device "HunterLab LabScan Spectralcolorimeter" of Hunter Lab Associates Laboratory, Inc., USA (Software SpecWare Software Version 1.01) and given by the device in %-values.

The compressive strength and the flexural strength are measured comparably to ISO 9917 respectively according to ISO 4049. For the measurement of the compressive strength 10 specimens (3×3×5 mm) of each material are prepared according to the manufacturer's recommendations and the measurements were carried out comparably to ISO 9917 using an universal testing machine (Zwick Z 010, crosshead speed 4 mm/min). The compressive strength is given is MPa. The measurement of the flexural strength is carried out according to ISO 4049 using an universal testing machine (Zwick Z 010, crosshead speed 2 mm/min). The flexural strength is given in MPa.

The halogenated aryl alkyl ether component (A) of the inventive composition can be represented by structural element (1):

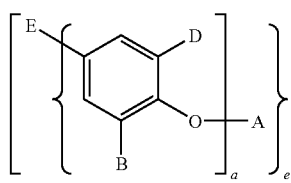

with independently selected from each other
A=(cyclo)alkyl or aryl (cyclo)alkyl or alkenyl with $C_1$-$C_{30}$, wherein C and/or H atoms can be substituted by Br, Cl, N or O;
B=H, Br Cl or allyl (preferably ally or Cl);
D=Br or Cl,
E=H, (cyclo)alkyl or aryl (cyclo)alkyl with $C_1$-$C_{100}$, wherein C and/or H atoms can be substituted by Br, Cl, N or O;
a=1, 2, 3 or 4, preferably 3, more preferably 1 or 2, together with e=1;
e=1, 2, 3 or 4, preferably 3, more preferably 2, together with a=1;
Br=bromine atom;
C=carbon atom;
Cl=chlorine atom;
H=hydrogen atom;
N=nitrogen atom;
O=oxygen atom.

Halogenated aryl alkyl ether component (A) of the inventive composition might have a comparably high refractive index together with a comparably low viscosity besides a comparably high lipophilicity, and a comparably high molecular weight.

Without wishing to be limited to any particular mechanism, it is thought that due to the aromatic moiety within the halogenated aryl alkyl ether component (A) the refractive index and the lipophilicity are comparably high which is of some importance for dental materials to achieve appropriate esthetics as well as to avoid staining and/or swelling by uptake of water and/or water soluble dyes (e.g. from coffee, tea, red wine).

Moreover, without wishing to be limited to any particular mechanism, it is thought that due to the comparably high molecular weight of halogenated aryl alkyl ether component (A) and/or different reactivities of used unsaturated moieties B within halogenated aryl alkyl ether component (A), the volume shrinkage of derived dental compositions is reduced in comparison to conventional (meth)acrylate composites.

In preferred embodiments halogenated aryl alkyl ether component (A) can be characterized by formulas (I-III) depending on the molecular structure of the halogenated aryl alkyl ether component (A) as well as on the numbers a or e of the aryl alkyl ether moieties of structural element (I) within the halogenated aryl alkyl ether component (A).

In a preferred embodiment halogenated aryl alkyl ether component (A) comprises structural element (1) only once and an alkenyl residue as moiety A (i.e. a=1 and e=1 and A=alkenyl with $C_1$-$C_{12}$, wherein C and/or H atoms can be substituted by Br, Cl, N, O) within the molecule and can be characterized by formula (I), wherein the indices are as defined above:

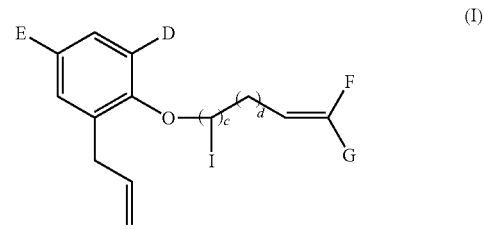

with independently selected from each other

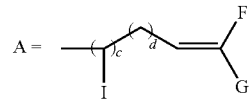

B=allyl
(wherein A and B refer to structural element (1) as described above)
D=Br or Cl,
E=H, Br or Cl (preferably Br or Cl)
F=H, alkyl or aryl with $C_1$-$C_6$, wherein C and/or H atoms can be substituted by Br, Cl, N or O (preferably H)
G=H, alkyl or aryl with $C_1$-$C_6$, wherein C and/or H atoms can be substituted by Br, Cl, N or O (preferably H)
I=alkyl ($C_1$-$C_2$)
a 1
c=0 or 1
d=1-10, up to 5, preferably up to 4, more preferably 2 or 3
e=1
wherein the indices are as defined above.

According to formula (I) the following structural formulas are preferred examples of halogenated aryl alkyl ether component (A):

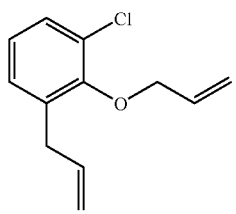

with: A=$C_3$, d=1, c=0, F=H, G=H, B=allyl, D=Cl, E=H

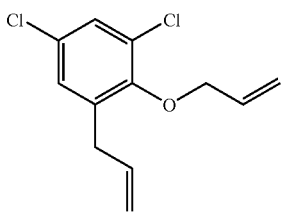

with: A=$C_3$, d=1, c=0, F=H, G=H, B=allyl, D=Cl, E=Cl

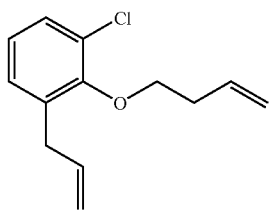

with: A=$C_4$, d=21, c=0, F=H, G=H, B=allyl, D=Cl, E=H

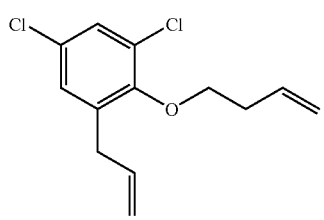

with: A=$C_4$, d=2, c=0, F=H, G=H, B=allyl, D=Cl, E=Cl

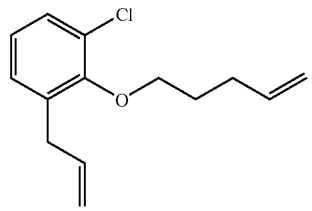

with: A=$C_5$, d=3, c=0, F=H, G=H, B=allyl, D=Cl, E=H

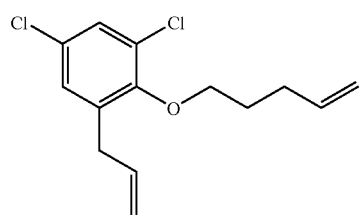

with: A=$C_5$, d=3, c=0, F=H, G=H, B=allyl, D=Cl, E=Cl

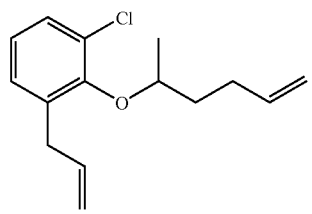

with: A=$C_6$, d=2, c=1, F=H, G=H, I=$C_1$, B=allyl, D=Cl, E=H

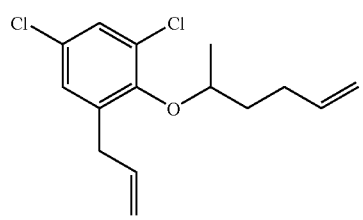

with: A=$C_6$, d=2, c=1, F=H, G=H, I=Cl, B=allyl, D=Cl, E=Cl

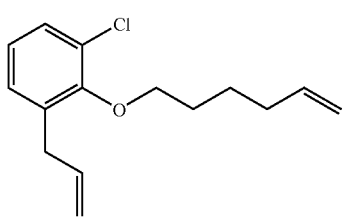

with: A=$C_6$, d=4, c=0, F=H, G=H, B=allyl, D=Cl, E=H

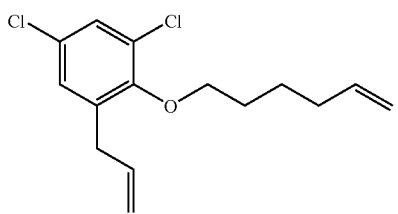

with: A=C$_6$, d=4, c=0, F=H, G=H, B=allyl, D=Cl, E=Cl

The following compounds are preferred examples of phenolic precursors (i) used according to scheme (I) for the synthesis of halogenated aryl alkyl ether component (A) fulfilling the requirements according to formula (I):

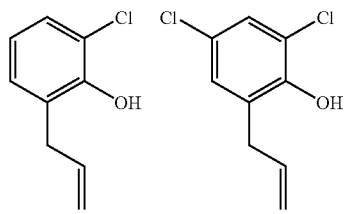

The following compounds are preferred examples of electrophile (ii) used according to scheme (I) for the synthesis of halogenated aryl alkyl ether component (A) fulfilling the requirements according to formula (I):

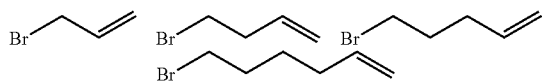

In a preferred embodiment the halogenated aryl alkyl ether component (A) comprises the structural element (1) more than once and the allyl residue as moieties B (i.e. a≧2 and e=1 and B=allyl) within the molecule and can be characterized by formula (II), wherein the indices are as defined above:

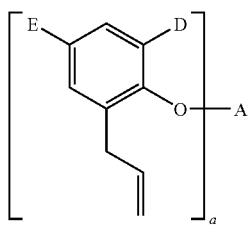

(II)

with independently selected from each other
A=(cyclo)alkyl or aryl (cyclo)alkyl with C$_1$-C$_{12}$, wherein C and/or H atoms can also be substituted by Br, Cl, N or O
B=allyl
D=Br or Cl, preferably Br, more preferably Cl
E=H, Br or Cl (preferably Br, more preferably Cl)
a=2, 3, 4, preferably 2 or 3
e=1,
wherein indices B and e refer to structural element (1) as described above.

According to formula (II) the following structural formulas are preferred examples of halogenated aryl alkyl ether component (A):

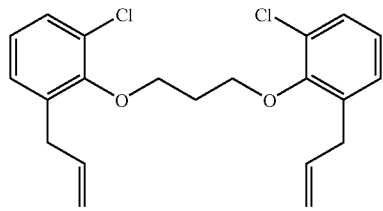

with: A=C$_3$, a=2, B=allyl, D=Cl, E=H

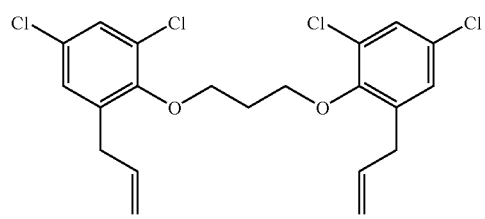

with: A=C3, a=2, B=allyl, D=Cl, E=H with H substituted by Cl

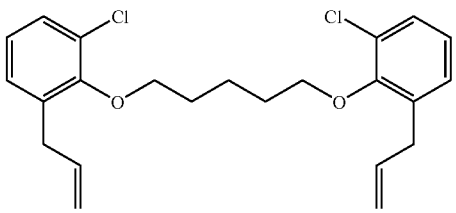

with: A=C5, a=2, B=allyl, D=Cl, E=H

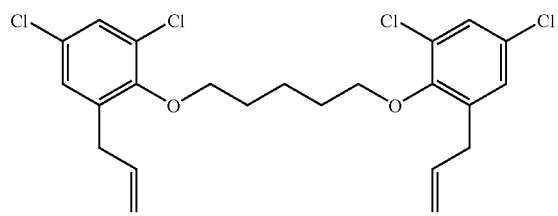

with: A=C$_5$, a=2, B=allyl, D=Cl, E=H with H substituted by Cl

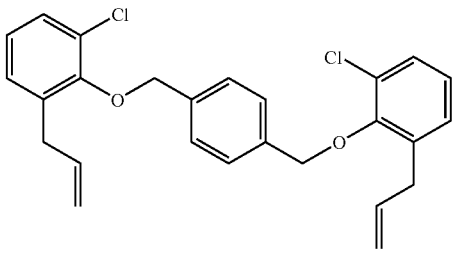

with: A=C$_8$, a=2, B=allyl, D=Cl, E=H with H substituted by Cl

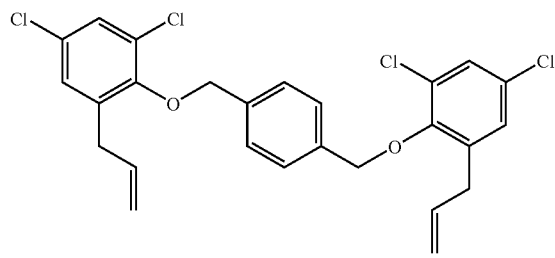

with: A=C$_9$, a=3, B=allyl, D=Cl, E=H

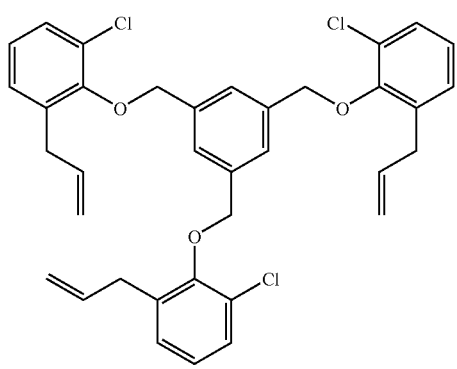

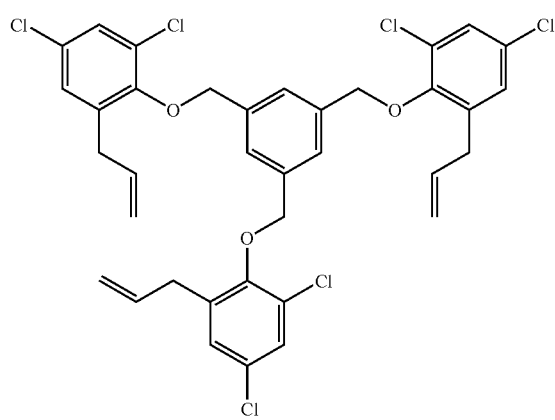

with: A=C$_9$, a=3, B=ally, D=Cl, E=H with H substituted by Cl

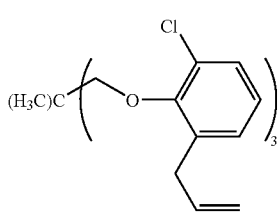

with: A=C$_5$, a=3, B=allyl, D=Cl, E=H

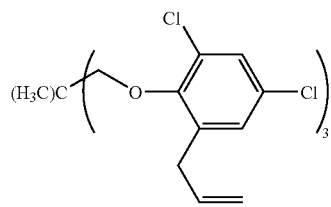

with: A=C$_5$, a=3, B=allyl, D=Cl, E=H with H substituted by Cl

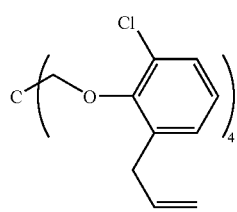

with: A=C$_5$, a=4, B=allyl, D=Cl, E=H

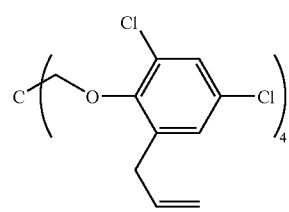

with: A=C$_5$, a=4, B=allyl, D=Cl, E=H with H substituted by Cl

The following compounds are preferred examples of phenolic precursors (i) used according to scheme (I) for the synthesis of halogenated aryl alkyl ether component (A) fulfilling the requirements according to formula (II):

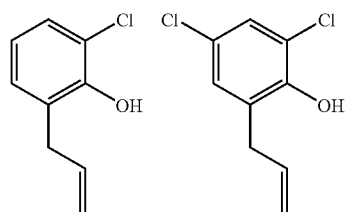

The following compounds are preferred examples of electrophile (ii) used according to scheme (I) for the synthesis of halogenated aryl alkyl ether component (A) fulfilling the requirements according to formula (II):

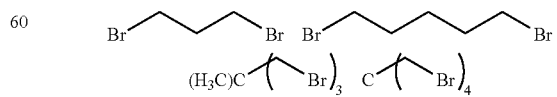

In another preferred embodiment halogenated aryl alkyl ether component (A) comprises structural element (1) more than once and alkenyl residues as moieties A (i.e. a=1 and $e \geq 2$ and A alkenyl with $C_1$-$C_{12}$, wherein C and/or H atoms can also be substituted by Br, Cl, N, O) within the molecule and can be characterized by formula (III), wherein the indices are as defined above:

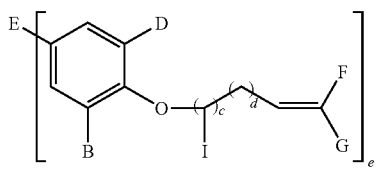

(III)

with independently selected from each other

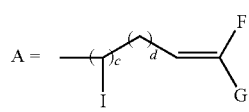

B=H, Br or Cl, preferably Br or Cl
D=Br or Cl, preferably Br or Cl
E=(cyclo)alkyl or aryl (cyclo)alkyl with $C_1$-$C_{80}$, wherein C and/or H atoms can be substituted by Br, Cl, N or O
F=H, alkyl or aryl with $C_1$-$C_6$, wherein C and/or H atoms can be substituted by Br, Cl, N or O (preferably H)
G=H, alkyl or aryl with $C_1$-$C_6$, wherein C and/or H atoms can be substituted by Br, Cl, N, O (preferably H)
I=alkyl ($C_1$-$C_2$)
a 1
c=0 or 1, preferably 0
d=1-10, up to 5, preferably up to 4, more preferably 2 or 3
e=2, 3 or 4.
wherein indices A and a refer to structural element (1) as described above.

According to formula (III) the following structural formulas are preferred examples of halogenated aryl alkyl ether component (A):

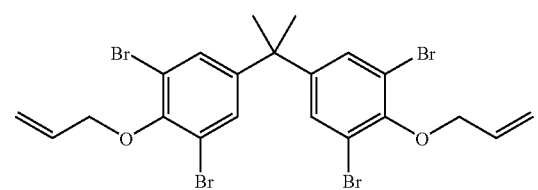

with: A=$C_3$, d=1, c=0, F=H, G=H, e=2, B=Br, D=Br, E=$C_3$

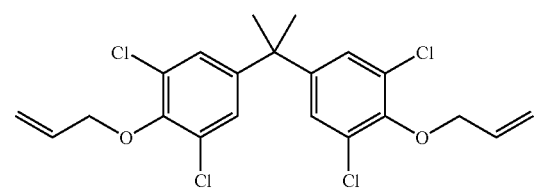

with: A=$C_3$, d=1, c=0, F=H, G=H, e=2, B=Cl, D=Cl, E=$C_3$

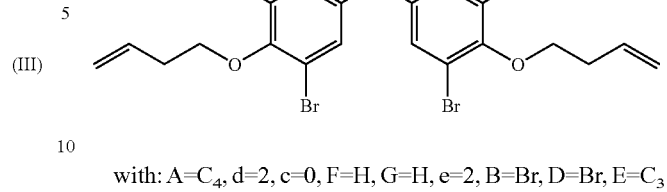

with: A=$C_4$, d=2, c=0, F=H, G=H, e=2, B=Br, D=Br, E=$C_3$

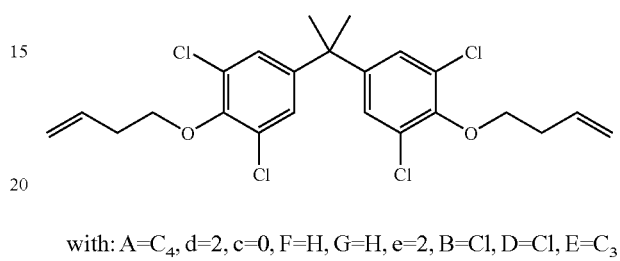

with: A=$C_4$, d=2, c=0, F=H, G=H, e=2, B=Cl, D=Cl, E=$C_3$

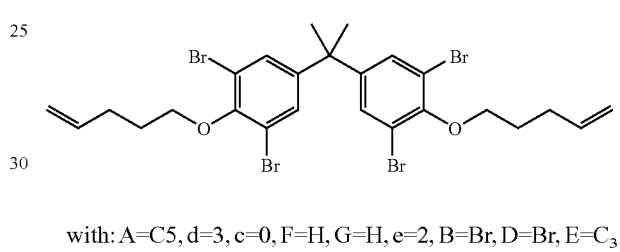

with: A=C5, d=3, c=0, F=H, G=H, e=2, B=Br, D=Br, E=$C_3$

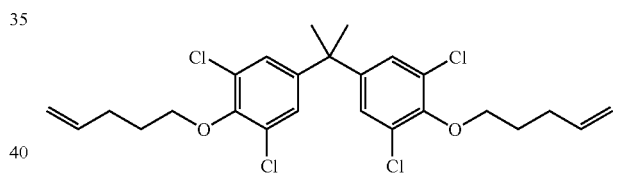

with: A=$C_5$, d=3, c=O, F=H, G=H, e=2, B=Cl, D=Cl, E=C3

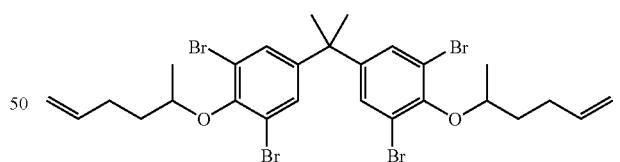

with: A=C6, d=2, c=1, F=H, G=H, I=$C_1$, e=2, B=Br, D=Br, E=C3

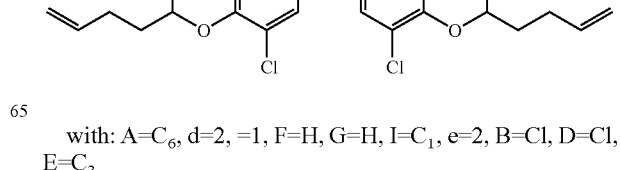

with: A=$C_6$, d=2, =1, F=H, G=H, I=$C_1$, e=2, B=Cl, D=Cl, E=$C_3$

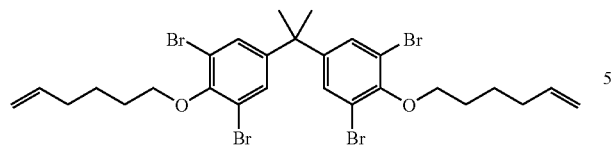
with: A=C$_6$, d=4, c=0, F=H, G=H, e=2, B=Br, D=Br, E=C$_3$
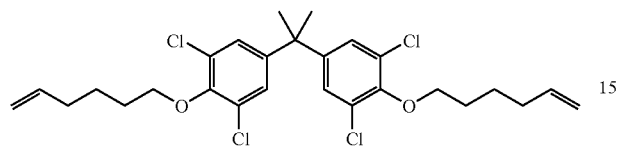
with: A=C$_6$, d=4, c=0, F=H, G=H, e=2, B=Cl, D=Cl, E=C3
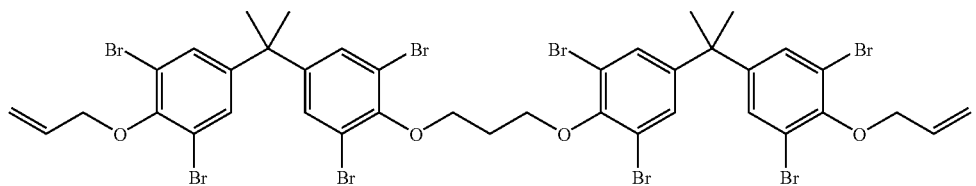
with: A=C$_3$, d=1, c=0, F=H, G=H, e=2, B=Br, D=Br, E=C$_{27}$ with C and H substituted in part by Br and 0
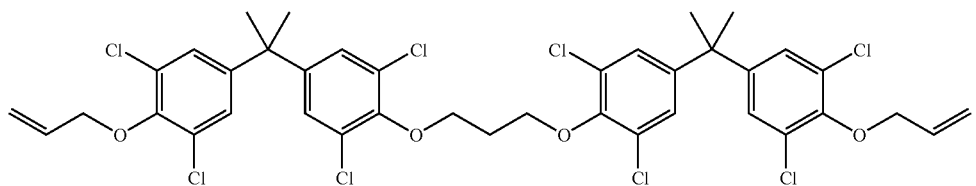
with: A=C$_3$, d=1, c=0, F=H, G=H, e=2, B=Cl, D=Cl, E=C$_{27}$ with C and H substituted in part by Cl and O
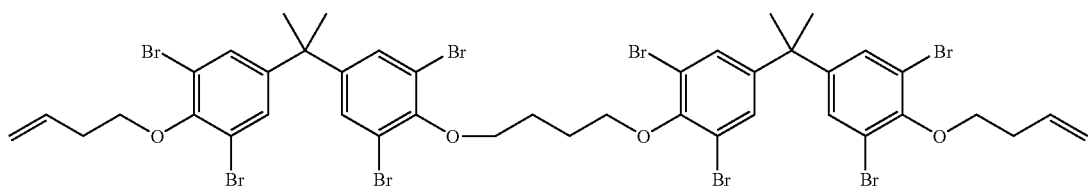
with: A=C$_4$, d=2, c=0, F=H, G=H, e=2, B=Br, D=Br, E=C$_{28}$ with C and H substituted in part by Br and O

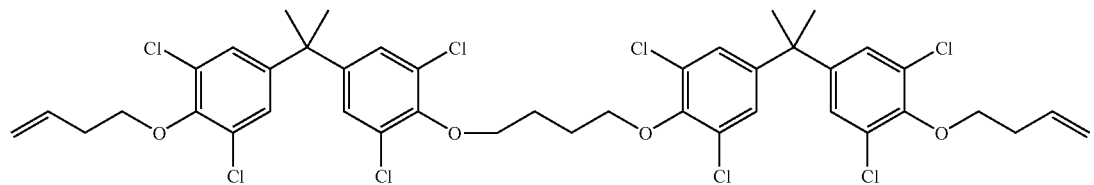

with: A=C$_4$, d=2, c=0, F=H, G=H, e=2, B=Cl, D=Cl, E=C$_{28}$ with C and H substituted in part by Cl and O with: A=C$_6$, d=2, c=1, F=H, G=H, I=C$_1$, e=2, B=Cl, D=Cl, E=C$_{30}$ with C and H substituted in part by Cl and O

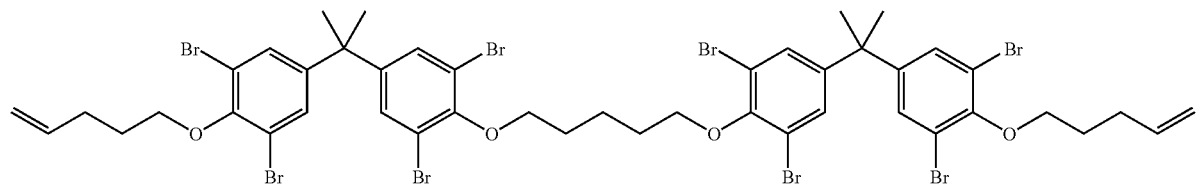

with: A=C5, d=3, c=0, F=H, G=H, e=2, B=Br, D=Br, E=C$_{29}$ with C and H substituted in part by Br and O

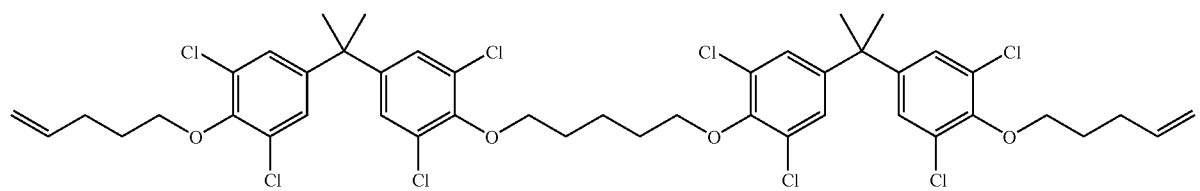

with: A=C$_5$, d=3, c=0, F=H, G=H, e=2, B=Cl, D=Cl, E=C$_{29}$ with C and H substituted in part by Cl and O

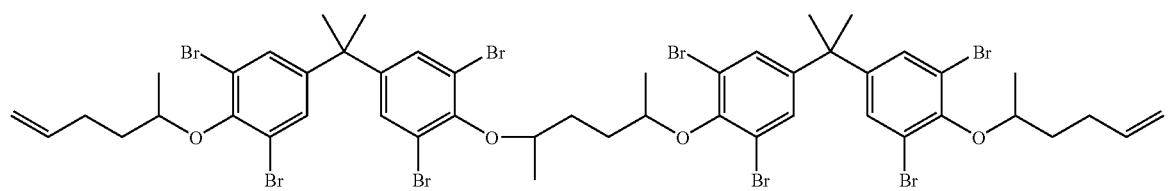

with: A=C6, d=2, c=1, F=H, G=H, I=C$_1$, e=2, B=Br, D=Br, E=C30 with C and H substituted in part by Br and O

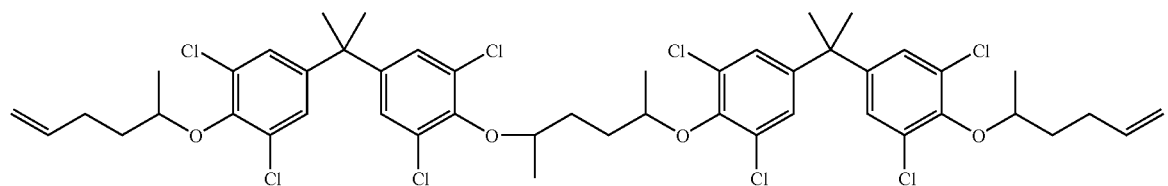

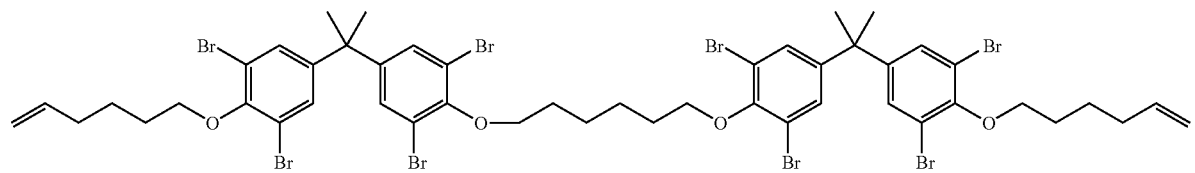

with: A=C$_6$, d=4, c=0, F=H, G=H, e=2, B=Br, D=Br, E=C$_{30}$ with C and H substituted in part by Br and O with: A=C$_4$, d=2, c=0, F=H, G=H, e=2, B=Br, D=Br, E=C$_{53}$ with C and H substituted in part by Br and O

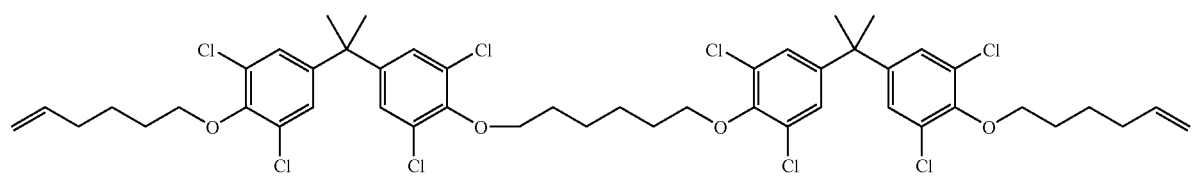

with: A=C6, d=4, c=0, F=H, G=H, e=2, B=Cl, D=Cl, E=C$_{30}$ with C and H substituted in part by Cl and O

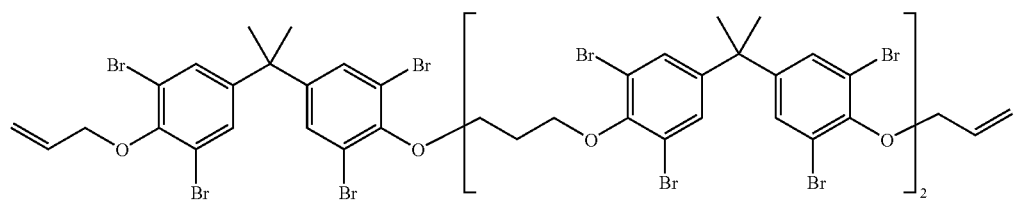

with: A=C$_3$, d=1, C=0, F=H, G=H, e=2, B=Br, D=Br, E=C$_{51}$ with C and H substituted in part by Br and O

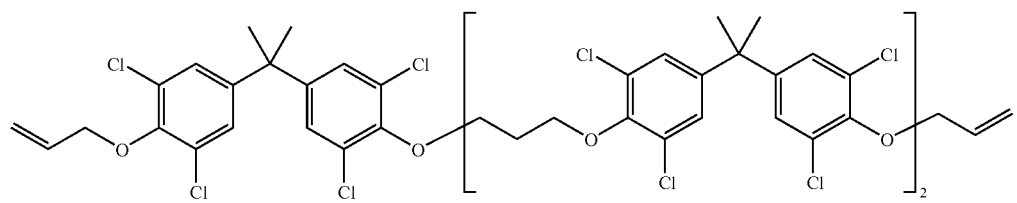

with: A=C$_3$, d=1, c=0, F=H, G=H, e=2, B=Cl, D=Cl, E=C$_{51}$ with C and H substituted in part by Cl and O

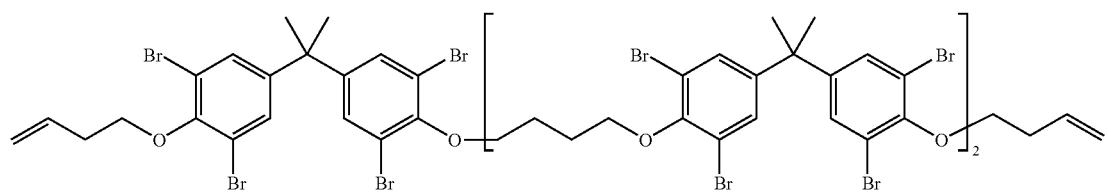

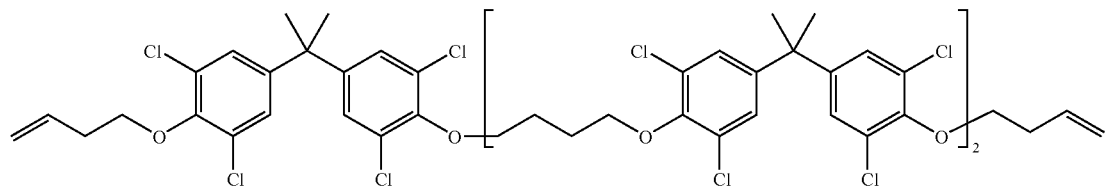

with: A=C$_4$, d=2, c=0, F=H, G=H, e=2, B=Cl, D=Cl, E=C53 with C and H substituted in part by Cl and O with: A=C$_6$, d=2, c=1, F=H, G=H, I=C$_1$, e=2, B=Cl, D=Cl, E=C$_{57}$ with C and H substituted in part by Cl and O

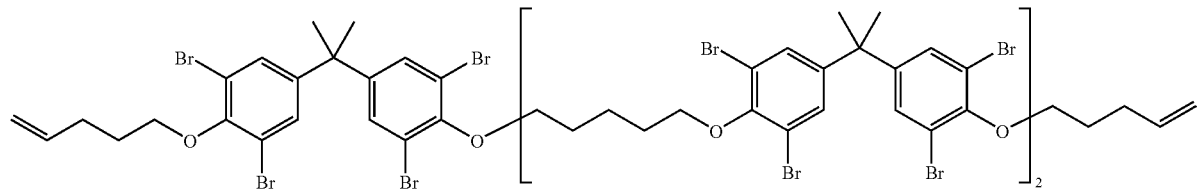

with: A=C$_5$, d=3, c=0, F=H, G=H, e=2, B=Br, D=Br, E=C$_{55}$ with C and H substituted in part by Br and O

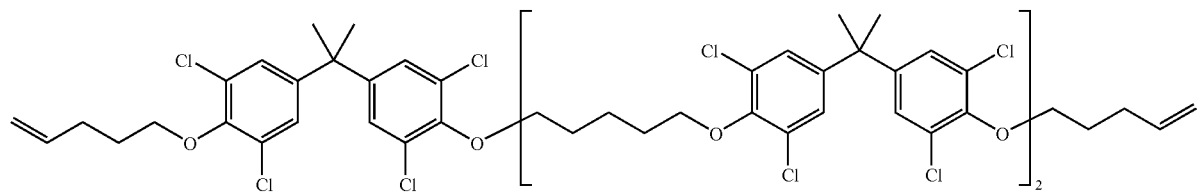

with: A=C$_5$, d=3, c=0, F=H, G=H, e=2, B=Cl, D=Cl, E=C$_{55}$ with C and H substituted in part by Cl and O

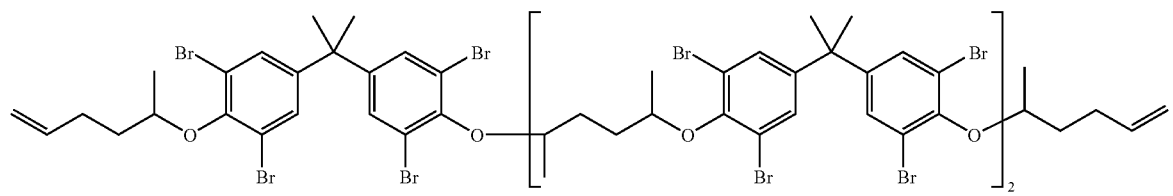

with: A=C$_6$, d=2, c=1, F=H, G=H, I=C$_1$, e=2, B=Br, D=Br, E=C$_{57}$ with C and H substituted in part by Br and O

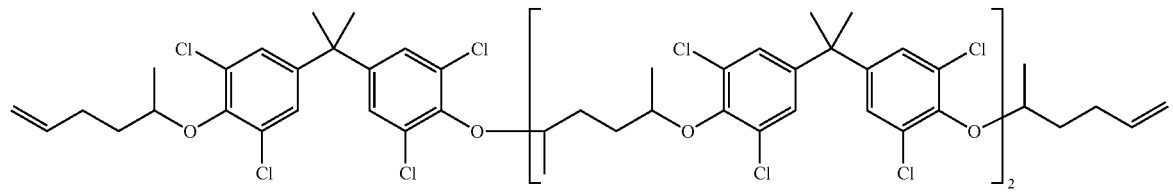

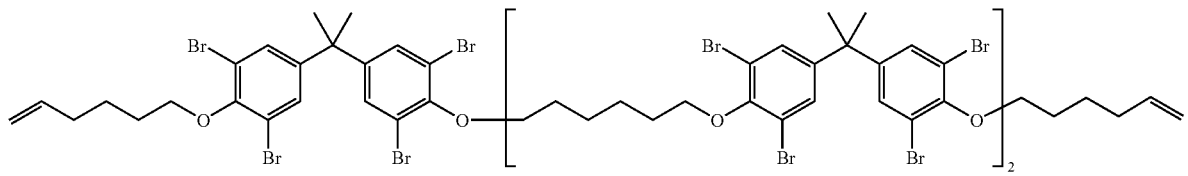

with: A=C$_6$, d=4, c=0, F=H, G=H, e=2, B=Br, D=Br, E=C$_{57}$ with C and H substituted in part by Br and O

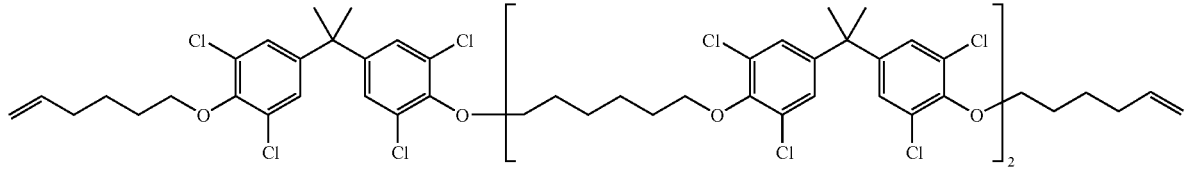

with: A=C$_6$, d=4, c=0, F=H, G=H, e=2, B=Cl, D=Cl, E=C$_{57}$ with C and H substituted in part by Cl and O The following compounds are preferred examples of phenolic precursors (i) used according to scheme (I) for the synthesis of halogenated aryl alkyl ether component (A) fulfilling the requirements according to formula (III):

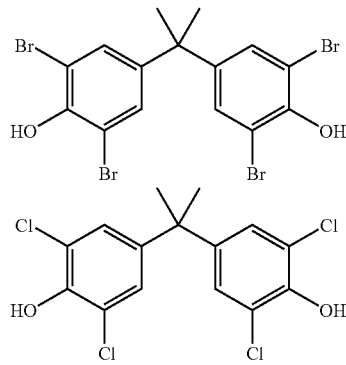

The following compounds are preferred examples of electrophile (ii) used according to scheme (I) for the synthesis of halogenated aryl alkyl ether component (A) fulfilling the requirements according to formula (III):

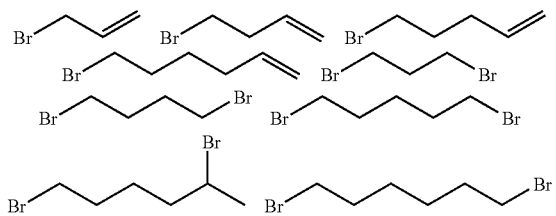

Useful Si—H functional components (B) can react with halogenated aryl alkyl ether component (A) via hydrosilylation reaction. Such Si—H functional components (B) can be organopolysiloxane and/or carbosilane derived compounds with Si-bonded hydrogen atoms. Si—H functional component (B) is preferably an organopolysiloxane with at least 2-Si-bonded hydrogen atoms per molecule and/or a carbosilane with at least 2 Si-bonded hydrogen atoms per molecule.

Useful initiators (C) can initiate curing of the halogenated aryl alkyl ether compound (A) of the composition in the presence of a Si—H functional compound (B). Such initiators can be light curing or chemical curing. Both types of initiators are well known to the skilled person in the art.

Representatives of such initiators are e.g. complexes of platinum (oxidation states 0 and/or +2), palladium (oxidation states 0 and/or +2), or rhodium (oxidation states 0 and/or +1) as described e.g. in Marciniec, B., Comprehensive Handbook on Hydrosilylation, p 8ff., Pergamon Press, Oxford, 1992 or e.g. in U.S. Pat. Nos. 5,145,886, 6,046,250, 6,376,569.

Initiator (C) is preferably a platinum complex which was prepared from hexachloroplatinum acid by reduction with tetramethyldivinyldisiloxane. These compounds are known. Other platinum compounds which accelerate addition cross-linking are also suitable. Suitable Platinum-siloxane complexes are described e.g. in U.S. Pat. Nos. 3,715,334, 3,775,352 and 3,814,730. The platinum catalyst is preferably used in quantities of 0.00005 to 0.5 wt.-%, particularly 0.0002 to 0.2 wt.-%, each calculated as elemental platinum and related to the overall weight of the material present regarding components (A) to (E).

To control the reactivity, it may be desirable to add an inhibitor which prevents premature cross-linking to elastomers. Such inhibitors are known and described, e.g. in U.S. Pat. No. 3,933,880. Examples of this are acetylenic unsaturated alcohols such as 3-Methyl-1-butyne-3-ol, 1-Ethynylcyclohexane-1-ol, 3,5-Dimethyl-1-hexyne-3-ol and 3-Methyl-1-pentyne-3-ol. Examples of inhibitors based on vinyl siloxane are 1,1,3,3-Tetramethyl-1,3-divinyl siloxane and poly-, oligo- and disiloxanes containing vinyl groups.

The composition of the present invention may also include filler (D), preferably inorganic fillers like quartz, ground glasses, silica gels as well as pyrogenic silicic acids and precipitation silicic acids or their granules. X-ray-opaque fillers are also preferably used, at least partially. These can, for example, be X-ray-opaque glasses, i.e. glasses which, for example, contain strontium, barium or lanthanum (e.g. according to U.S. Pat. No. 3,971,754) Some of the fillers may contain an X-ray-opaque additive, such as yttrium trifluoride, strontium hexafluorozirconate or fluorides of the rare earth metals (e.g. according to EP 0 238 025 A1). For better incorporation into the polymer matrix, it may be advantageous to hydrophobize the inorganic fillers. Typical hydrophobization agents include silanes, e.g. (5-Hexenyl)trimethoxysilane or [2-(3-Cyclohexenyl)-ethyl]trimethoxysilane. The fillers preferably have an average grain size <20 µm, particularly <5 µm and more particularly <2 µm and an upper grain limit of 150 µm, particularly 70 µm and more particularly 25 µm. Such fillers can be present in amounts of from about 3 to about 90 weight percent, especially about 25 to about 80 or about 50 to about 75 wt.-% of the composition.

Non-reinforcing fillers may also be used in the invention such as quartz, cristobalite, calcium silicate, diatomaceous earth, zirconium silicate, montmorillonite such as bentonite, zeolite, including moleculer sieves such as sodium aluminium silicate, metal oxide powder such as aluminium or zinc oxide or their mixed oxides, barium sulphate, calcium carbonate, plaster, glass and plastic powder.

Suitable fillers also include reinforcing fillers such as e.g. pyrogenic or precipitated silicic acid and silica aluminium mixed oxides. The above mentioned fillers can be hydrophobized, for example by treatment with organosilanes or siloxanes or by the etherification of hydroxyl groups to alkoxy groups. One type of filler or also a mixture of at least two fillers can be used.

A combination of reinforcing and non-reinforcing fillers is particularly preferred. In this respect, the quantity of reinforcing fillers can vary from about 1 to about 10 wt.-%, and in particular, from about 2 to about 5 wt.-%.

The difference in the named overall ranges, i.e. about 2 to about 89 wt.-% is accounted for by non-reinforcing fillers.

Pyrogenically-prepared highly-disperse, silicic acids which have preferably been hydrophobized by surface treatment are preferred as reinforcing fillers. The surface treatment can be carried out, e.g. with dimethyldichlorosilane, hexamethyldisilazane, tetramethylcyclotetrasiloxane or polymethylsiloxane.

Particularly preferred non-reinforcing fillers are quartzes, cristobalites, calcium carbonate and sodium aluminium silicates which can be surface-treated. The surface treatment can generally be carried out with the same methods as described in the case of the strengthening fillers.

Optionally additives (E) like stabilizers, modifiers, dyes, pigments, thixotropic agents, flow improvers, or thinning agents, polymeric thickeners, surfactants, and diluting agent (s) can be added alone or in admixture.

The above described halogenated aryl alkyl ether component (A) can be used as monomer in dental compositions that are curable preferably via hydrosilylation reaction of unsaturated groups, especially terminal olefinic groups.

The dental composition of the invention can be used e.g. as dental filling material, crown and bridge material, veneer material, inlay or onlay.

The invention also relates to a method of using the halogenated aryl alkyl ether component (A) for preparing a dental material in a process comprising the steps of
 a) providing a dental composition comprising halogenated aryl alkyl ether component (A);
 b) applying the dental composition to a surface;
 c) curing the dental composition.

The surface is usually a surface of a tooth, a crown or a bridge.

The dental compositions of the invention can be provided as a 1 part mixture or as a 2 part mixture. This usually depends on the initiator used. If the initiator is light curing, the dental composition can be provided as a 1 part mixture, if the initiator is redox curing, the dental composition should be provided as a 2 part mixture.

Therefore, the present invention also relates to a kit of parts, comprising base part (I) and catalyst part (II), wherein base part (I) comprises halogenated aryl alkyl ether component (A), Si—H functional component (B), and filler (D), and the catalyst part (II) comprises initiator (C), and wherein component (E) is present either in the base part or the catalyst part or in the base part and the catalyst part.

The dental compositions of the invention is usually packaged in a container or cartridge, preferably in a dental compule. Examples of such computes are described in U.S. Pat. Nos. 5,322,440 A1 or 4,391,590 or 5,165,890.

The present invention also relates to a method of producing a curable dental composition comprising the steps
 a) providing components (A), (B), (C), optionally (D) and optionally (E);
 b) mixing the components of step a),
 wherein component (A) is obtainable via an etherification reaction.

The etherification reaction comprises reacting phenolic precursor (i) and electrophile (ii) as describe above.

The invention is hereinafter described by examples. The examples are for illustrative purpose only and not intended to limit the invention.

The compounds listed in table 1 were prepared according to the references listed above and their refractive index and viscosity measured.

TABLE 1

| Examples of Compounds | Refractive Index | Viscosity [mPa * s] | Molecular Weight [g/mol] |
|---|---|---|---|
| Reference Compound 1: 1,3,5,7-Tetramethyl-cyclotetrasiloxane | 1.387 | 100 | 240.5 |
| Reference Compound 2: 1,3,5,7-Tetramethyl-1,3,5,7-tetravinyl-cyclotetrasiloxane | 1.434 | 400 | 344.7 |
| Reference Compound 3: Poly(ethyleneglycol) (average Mn 600) diallylether | 1.464 | 30 | 680.1 |
| Example Compound 1: Allyl-(2-allyl-4,6-dichloro-phenyl)-ether | 1.545 | 5 | 243.1 |
| Example Compound 2: 1,5-Bis(2-allyl-4,6-dichloro-phenoxy)-pentane | 1.564 | 150 | 474.3 |

Dental compositions containing the halogenated aryl alkyl ether compound according to the invention as well as dental compositions containing state of the art reference compounds were prepared and their opacity evaluated.

TABLE 2

| Amounts in %-Weight | Examples of Dental Compositions | | |
|---|---|---|---|
| | 1 | 2 | 3 |
| Reference Compound 1 | 20.3 | 19.5 | 11.7 |
| Reference Compound 2 | 30.5 | | |
| Reference Compound 3 | | 9.8 | 11.7 |
| Example Compound 1 | | 29.3 | |
| Example Compound 2 | | | 35.2 |
| (1,3,5,7-Tetramethyl-1,3,5,7-tetravinyl)platinum(0) | 1.4 | 1.4 | 1.4 |
| Quartz, mean particle size <2 μm | 30.4 | 35.0 | 35.0 |
| Hydrophobized Highly-Disperse Silicic Acid | 17.4 | 5.0 | 5.0 |
| Opacity [%] | 95.6 | 80.9 | 85.8 |
| Exact Height of Specimen [mm] | (3.6) | (3.6) | (3.6) |

The invention claimed is:

1. A dental composition comprising
   a) halogenated aryl alkyl ether component comprising
      at least 1 aryl alkyl ether moiety,
      at least 1 halogen atom attached to each aryl residue of the aryl alkyl ether moieties, and
      at least 2 unsaturated moieties;
   b) an Si—H functional component; and
   c) an initiator;
   wherein the halogenated aryl alkyl ether component is represented by the following formula (I):

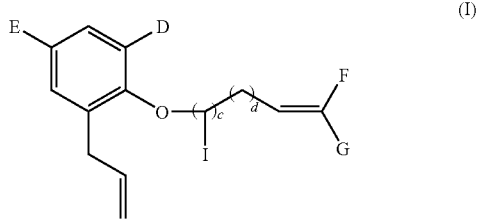

wherein, independently selected from each other,
D is Br or Cl;
E is H, Br or Cl;
F is H or alkyl or aryl, wherein C and/or H atoms can be substituted by Br, Cl, N or O;
G is H or alkyl or aryl, wherein C and/or H atoms can be substituted by Br, Cl, N or O;
I is a $C_1$ to $C_2$ alkyl;
c is 0 or 1; and
d is 1 to 10.

2. A container or cartridge filled with a dental composition of claim 1.

3. The container or cartridge of claim 2 wherein the dental composition further comprises a filler.

4. The container or cartridge of claim 3 wherein the dental composition further comprises an additive selected from modifiers, dyes, pigments, thixotropic agents, flow improvers, polymeric thickeners, surfactants, odorous substances, diluting agents, and flavourings.

5. The container or cartridge of claim 3, wherein the filler comprises reinforcing or non-reinforcing fillers or a combination of both.

6. The container or cartridge of claim 4, wherein:
   the halogenated aryl alkyl is present in an amount of at least about 1% by weight,
   the Si—H functional component is present in an amount of at least about 1% by weight,
   the inititator is present in an amount of at least about 0.00005% by weight, calculated as elemental metal,
   the filler is present in an amount of at least about 3% by weight, and
   the additive is present in an amount of less than about 25% by weight,
   with respect to the dental composition, upon curing.

7. The container or cartridge of claim 2, wherein the halogenated aryl alkyl ether component has a refractive index equal to or above about 1.530.

8. The container or cartridge of claim 2, wherein the halogenated aryl alkyl ether component has a viscosity equal to or above about 0.1 Pa*s.

9. The container or cartridge of claim 2, wherein the halogenated aryl alkyl ether component has a molecular mass equal to or above about 400.

10. The container or cartridge of claim 2, wherein the opacity of the dental composition, upon curing, is equal to or above about 10%.

11. The container or cartridge of claim 2, wherein the compressive strength of the dental composition, upon curing, is equal to or above about 150 MPa.

12. The container or cartridge of claim 2, wherein the flexural strength of the dental composition, upon curing, is equal to or above about 50 MPa.

13. The container or cartridge of claim 2, wherein the Si—H functional component is selected from organopolysiloxane and/or carbosilane derived components with Si-bonded hydrogen atoms.

14. The container or cartridge of claim 2, wherein the initiator comprises a light miring initiator or a chemical curing initiator or a combination of both.

15. A dental material selected from a dental filling material, a crown or bridge material, a veneer material, an inlay and/or an onlay, wherein the dental material comprises the dental composition of claim 1.

16. A dental composition comprising
    a) halogenated aryl alkyl ether component comprising
       at least 1 aryl alkyl ether moiety,
       at least 1 halogen atom attached to each aryl residue of the aryl alkyl ether moieties, and
       at least 2 unsaturated moieties;
    b) an Si—H functional component; and
    c) an initiator;
    wherein the halogenated aryl alkyl ether component is represented by the following formula (II):

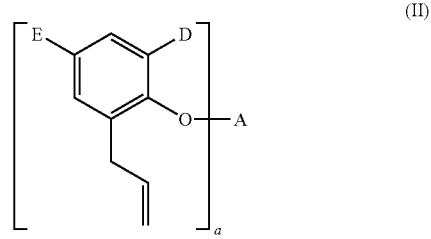

wherein, independently selected from each other,
A is (cyclo)alkyl or aryl (cyclo)alkyl, wherein C and/or H atoms can be substituted by Br, Cl, N or O;
D is Br or Cl;
E is H, Br or Cl; and
a is 2, 3 or 4.

17. A container or cartridge filled with a dental composition of claim 16.

18. A dental material selected from a dental filling material, a crown or bridge material, a veneer material, an inlay and/or an onlay, wherein the dental material comprises the dental composition of claim 16.

19. A dental composition comprising
   a) halogenated aryl alkyl ether component comprising
      at least 1 aryl alkyl ether moiety,
      at least 1 halogen atom attached to each aryl residue of the aryl alkyl ether moieties, and
      at least 2 unsaturated moieties;
   b) an Si—H functional component; and
   c) an initiator;
   wherein the halogenated aryl alkyl ether component is represented by the following formula (III):

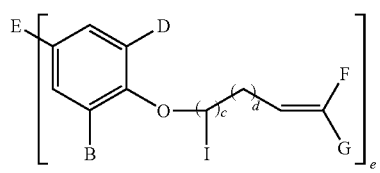

(III)

wherein, independently selected from each other,
B is H, Br or Cl;
D is Br or Cl;
E is (cyclo)alkyl or aryl (cyclo)alkyl, wherein C and/or H atoms can be substituted by Br, Cl, N or O;
F is H or alkyl or aryl, wherein C and/or H atoms can be substituted by Br, Cl, N or O;
G is H or alkyl or aryl, wherein C and/or H atoms can be substituted by Br, Cl, N or O;
I is a $C_1$ to $C_2$ alkyl;
c is 0 or 1;
d is 1 to 10; and
e is 2, 3 or 4.

20. A container or cartridge filled with a dental composition of claim 19.

21. A dental material selected from a dental filling material, a crown or bridge material, a veneer material, an inlay and/or an onlay, wherein the dental material comprises the dental composition of claim 19.

22. A dental composition comprising
   a) halogenated aryl alkyl ether component comprising
      at least 1 aryl alkyl ether moiety,
      at least 1 halogen atom attached to each aryl residue of the aryl alkyl ether moieties, and
      at least 2 unsaturated moieties;
   b) an Si—H functional component; and
   c) an initiator;
   wherein halogenated aryl alkyl ether component is selected from:

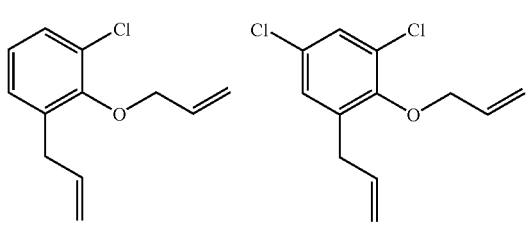

-continued

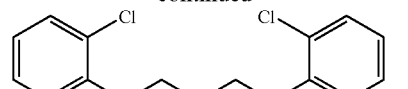
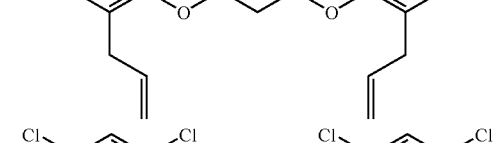
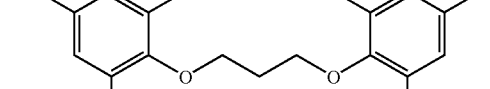
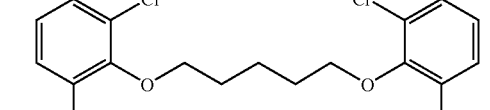
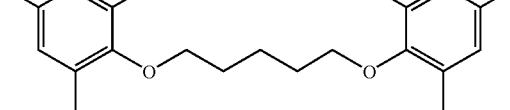
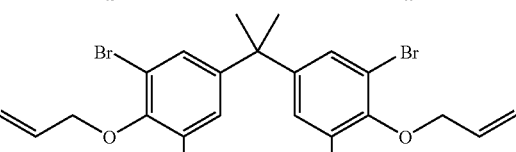
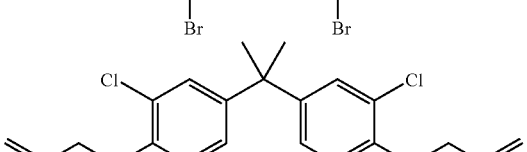
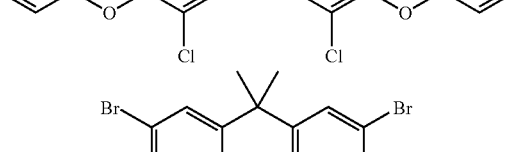
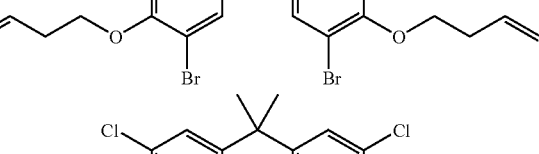
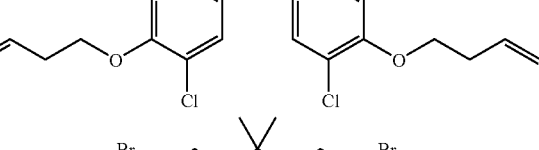
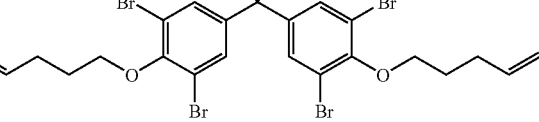

-continued

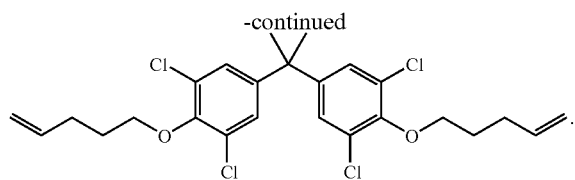

23. A container or cartridge filled with a dental composition of claim 22.

24. A dental material selected from a dental filling material, a crown or bridge material, a veneer material, an inlay and/or an onlay, wherein the dental material comprises the dental composition of claim 22.

25. A method of producing a curable dental composition, the method comprising:
    a) providing a halogenated aryl alkyl ether component comprising:
       at least 1 aryl alkyl ether moiety,
       at least 1 halogen atom attached to each aryl residue of the aryl alkyl ether moieties, and
       at least 2 unsaturated moieties;
    b) providing an Si—H functional component;
    c) providing an initiator;
    d) mixing the components of a), b), and c), wherein the halogenated aryl alkyl ether component is obtainable via an etherification reaction comprising reacting a phenolic precursor and an electrophile;
    wherein the phenolic precursor is selected from the group consisting of

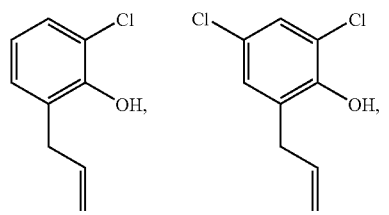

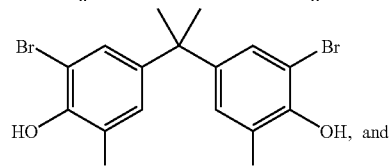

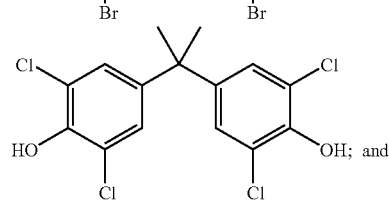

wherein the electrophile is selected from the group consisting of:

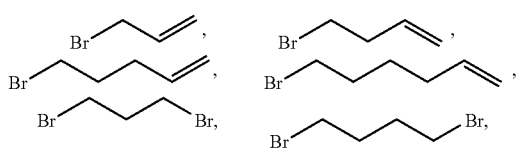

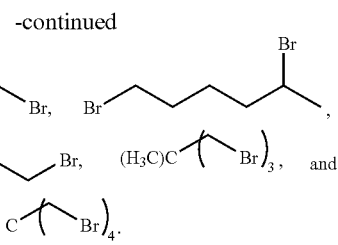

26. A kit of parts comprising a base part and a catalyst part, wherein the base part comprises a halogenated aryl alkyl ether component comprising:
    a) halogenated aryl alkyl ether component comprising:
       at least 1 aryl alkyl ether moiety,
       at least 1 halogen atom attached to each aryl residue of the aryl alkyl ether moieties, and
       at least 2 unsaturated moieties;
    b) an Si—H functional component that reacts with the halogenated aryl alkyl ether component via a hydrosilylation reaction; and
    c) a filler,
    wherein the halogenated aryl alkyl ether component is represented by the following formula (I):

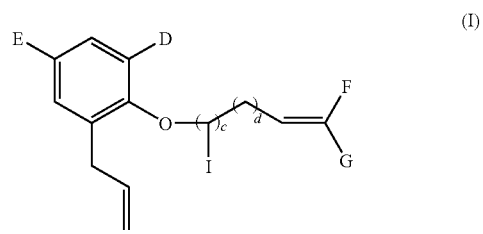

wherein, independently selected from each other,
D is Br or Cl;
E is H, Br or Cl;
F is H or alkyl or aryl, wherein C and/or H atoms can be substituted by Br, Cl, N or O;
G is H or alkyl or aryl, wherein C and/or H atoms can be substituted by Br, Cl, N or O;
I is a $C_1$ to $C_2$ alkyl;
c is 0 or 1; and
d is 1 to 10; and
    the catalyst part comprises an initiator that initiates curing of the halogenated aryl alkyl ether component in the presence of the Si—H functional component,
    wherein an additive component is present either in the base part or the catalyst part or in the base part and the catalyst part.

27. A kit of parts comprising a base part and a catalyst part, wherein the base part comprises a halogenated aryl alkyl ether component comprising:
    a) halogenated aryl alkyl ether component comprising:
       at least 1 aryl alkyl ether moiety,
       at least 1 halogen atom attached to each aryl residue of the aryl alkyl ether moieties, and
       at least 2 unsaturated moieties;
    b) an Si—H functional component that reacts with the halogenated aryl alkyl ether component via a hydrosilylation reaction; and
    c) a filler, wherein the halogenated aryl alkyl ether component is represented by the following formula (II):

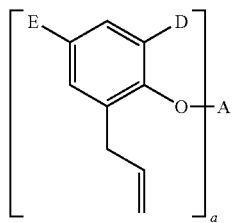

(II)

wherein, independently selected from each other,
A is (cyclo)alkyl or aryl (cyclo)alkyl, wherein C and/or H atoms can be substituted by Br, Cl, N or O;
D is Br or Cl;
E is H, Br or Cl; and
a is 2, 3 or 4; and
and the catalyst part comprises an initiator that initiates curing of the halogenated aryl alkyl ether component in the presence of the Si—H functional component,
wherein an additive component is present either in the base part or the catalyst part or in the base part and the catalyst part.

28. A kit of parts comprising a base part and a catalyst part, wherein the base part comprises a halogenated aryl alkyl ether component comprising:
a) halogenated aryl alkyl ether component comprising:
at least 1 aryl alkyl ether moiety,
at least 1 halogen atom attached to each aryl residue of the aryl alkyl ether moieties, and
at least 2 unsaturated moieties;
b) an Si—H functional component that reacts with the halogenated aryl alkyl ether component via a hydrosilylation reaction; and
c) a filler,
wherein the halogenated aryl alkyl ether component is represented by the following formula (III):

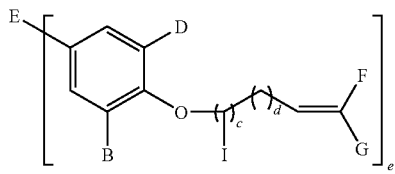

(III)

wherein, independently selected from each other,
B is H, Br or Cl;
D is Br or Cl;
E is (cyclo)alkyl or aryl (cyclo)alkyl, wherein C and/or H atoms can be substituted by Br, Cl, N or O;
F is H or alkyl or aryl, wherein C and/or H atoms can be substituted by Br, Cl, N or O;
G is H or alkyl or aryl, wherein C and/or H atoms can be substituted by Br, Cl, N or O;
I is a $C_1$ to $C_2$ alkyl;
c is 0 or 1;
d is 1 to 10; and
e is 2, 3 or 4; and
and the catalyst part comprises an initiator that initiates curing of the halogenated aryl alkyl ether component in the presence of the Si—H functional component,
wherein an additive component is present either in the base part or the catalyst part or in the base part and the catalyst part.

29. A kit of parts comprising a base part and a catalyst part, wherein the base part comprises a halogenated aryl alkyl ether component comprising:
a) halogenated aryl alkyl ether component comprising:
at least 1 aryl alkyl ether moiety,
at least 1 halogen atom attached to each aryl residue of the aryl alkyl ether moieties, and
at least 2 unsaturated moieties;
b) an Si—H functional component that reacts with the halogenated aryl alkyl ether component via a hydrosilylation reaction; and
c) a filler,
wherein the halogenated aryl alkyl ether component is selected from:

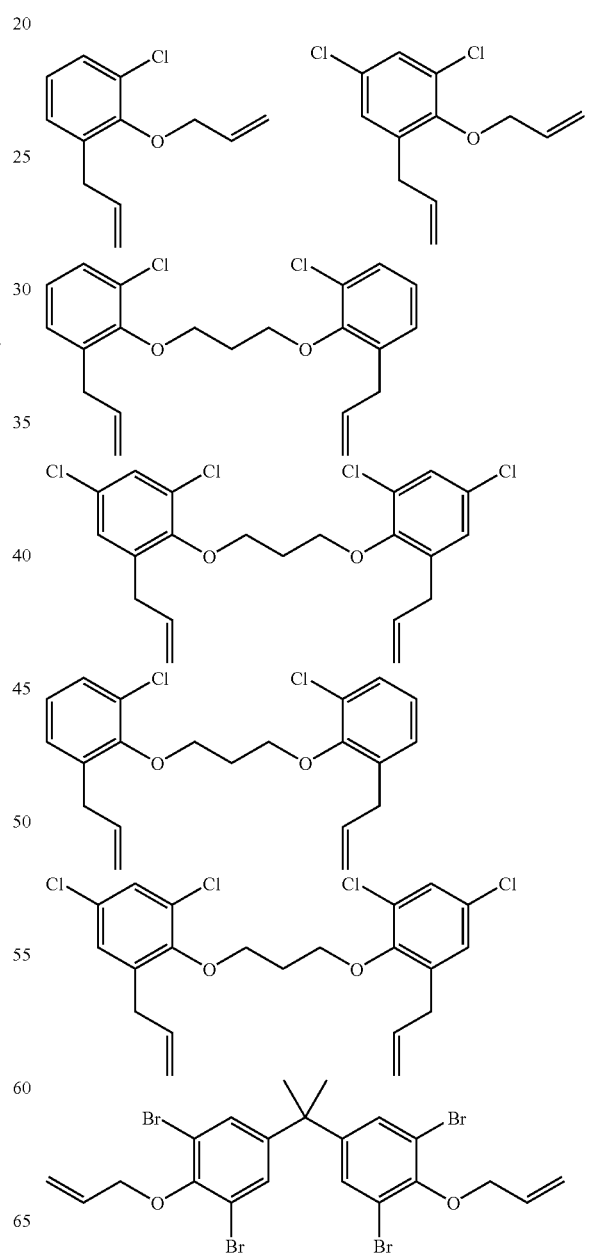

-continued
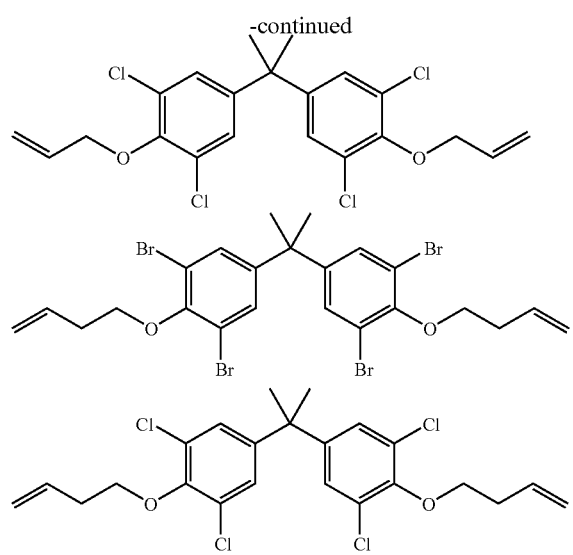
-continued
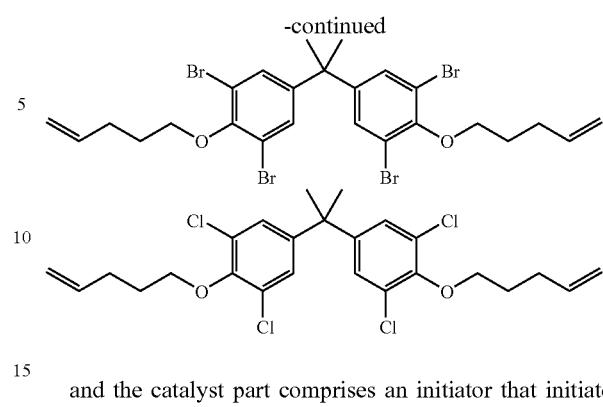
and the catalyst part comprises an initiator that initiates curing of the halogenated aryl alkyl ether component in the presence of the Si—H functional component,
wherein an additive component is present either in the base part or the catalyst part or in the base part and the catalyst part.
* * * * *

UNITED STATES PATENT AND TRADEMARK OFFICE
CERTIFICATE OF CORRECTION

PATENT NO. : 7,825,167 B2
APPLICATION NO. : 11/572067
DATED : November 2, 2010
INVENTOR(S) : Adrian Eckert It is certified that error appears in the above-identified patent and that said Letters Patent is hereby corrected as shown below:

Title Page
Item 56, Foreign Patent Documents, delete "EP 0451709 A2 10/1991" and insert -- EP 0451702 A2 10/1991 --.

Column 1
Line 36, Delete "lmethylethyl)benzene." and insert -- 1methylethyl)benzene. --, therefor.
Line 49, Delete "siiloxane" and insert -- siloxane --, therefor.
Line 58, Delete "visclosity." and insert -- viscosity. --, therefor.

Column 5
Line 23, Delete "know" and insert -- known --, therefor.

Column 7
Line 11, Delete "a 1" and insert -- a=1 --, therefor.
Line 55, Delete "d=21," and insert -- d=2, --, therefor.

Column 8
Line 52, Delete "I=C1," and insert -- I=$C_1$, --, therefor.

Column 10
Line 27, Delete "A=C3," and insert -- A=$C_3$, --, therefor.
Line 40, Delete "A=C5," and insert -- A=$C_5$, --, therefor.

Column 1
Line 1-2, After "E=H" delete "with H substituted by Cl".
Line 16, Delete "with: A=$C_9$, a=3, B=allyl, D=Cl, E=H" and insert -- with: A=$C_8$, a=2, B=allyl, D=Cl, E=H with H substituted by Cl --, therefor.

Signed and Sealed this
Fourteenth Day of June, 2011

David J. Kappos
*Director of the United States Patent and Trademark Office*

Column 11

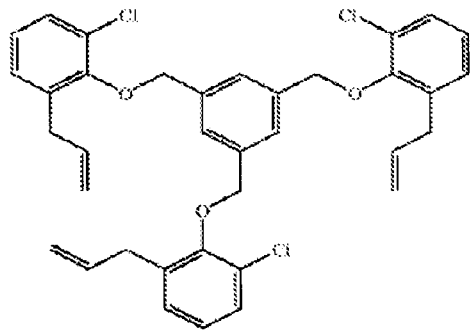

Line 34, Below " " insert -- with: A=C9, a=3, B=allyl, D=Cl, E=H --.

Column 13
Line 35, Delete "a 1" and insert -- a=1 --, therefor.

Column 2
Line 33, Delete "A=C5," and insert -- A=$C_5$, --, therefor.
Line 44, Delete "E=C3" and insert -- E=$C_3$ --, therefor.
Line 55, Delete "A=C6," and insert -- A=$C_6$, --, therefor.
Line 56, Delete "E=C3" and insert -- E=$C_3$ --, therefor.
Line 66, Delete "=1," and insert -- c=1, --, therefor.

Column 17
Line 25, Delete "A=C5," and insert -- A=$C_5$, --, therefor.
Below 4th Structure, Delete "A=C6," and insert -- A=$C_6$, --, therefor.
Below 4th Structure, Delete "E=C30" and insert -- E=$C_{30}$ --, therefor.

Column 19
Below 2nd Structure, Delete "A=C6," and insert -- A=$C_6$, --, therefor.
Below 3rd Structure, Delete "C=0," and insert -- c=0, --, therefor.

Column 21
Below 1st Structure, Delete "E=C53" and insert -- E=$C_{53}$ --, therefor.

Column 25
Line 16, Delete "moleculer" and insert -- molecular --, therefor.

Column 26
Line 30, Delete "computes" and insert -- compules --, therefor.

Column 27
Line 50, In Claim 1, delete "1to 10." and insert -- 1 to 10. --, therefor.

Column 28

Line 1, In Claim 6, delete "inititator" and insert -- initiator --, therefor.
Line 31, In Claim 14, delete "miring" and insert -- curing --, therefor.

Column 33
Line 21, In Claim 27, before "the" delete "and".
Line 65, In Claim 28, before "the" delete "and".